United States Patent [19]

Mercado et al.

[11] Patent Number: 4,783,333

[45] Date of Patent: Nov. 8, 1988

[54] COSMETIC CONTAINING COLOR PARTICLES

[75] Inventors: Clara Mercado, Aberdeen; Debra Verdon, Leonardo, both of N.J.

[73] Assignee: Charles of the Ritz Group, Ltd., New York, N.Y.

[21] Appl. No.: 149,909

[22] Filed: Jan. 27, 1988

Related U.S. Application Data

[63] Continuation of Ser. No. 840,223, Mar. 17, 1986, abandoned.

[51] Int. Cl.⁴ .................... A61K 7/021; A61K 31/74; A61K 7/04
[52] U.S. Cl. ........................................ 424/63; 424/64; 424/69; 514/844; 514/847
[58] Field of Search ............................ 424/63, 64, 69; 514/844, 847

[56] References Cited

U.S. PATENT DOCUMENTS

| | | | |
|---|---|---|---|
| 4,014,995 | 3/1977 | Juliano et al. | 424/63 |
| 4,137,302 | 1/1979 | Humbert et al. | 424/64 |
| 4,323,554 | 4/1982 | Bernhard | 424/63 |
| 4,423,031 | 12/1983 | Murui et al. | 424/63 |
| 4,492,686 | 1/1985 | Guillon | 424/69 |
| 4,534,963 | 8/1985 | Gordon | 424/63 |
| 4,650,672 | 3/1987 | Yagita et al. | 424/69 |

Primary Examiner—Ronald W. Griffin
Attorney, Agent, or Firm—Lerner, David, Littenberg, Krumholz & Mentlik

[57] ABSTRACT

A facial cosmetic is provided which may be in the form of an eye shadow or blusher which contains stones or pearls formed of color-coated titanated mica particles, together with dry and wet binder and feel enhancer, such as volatile silicone.

10 Claims, No Drawings

COSMETIC CONTAINING COLOR PARTICLES

This is a continuation of application Ser. No. 840,223 filed Mar. 17, 1986, now abandoned.

FIELD OF THE INVENTION

The present invention relates to a cosmetic, such as an eye shadow or blusher, which contains color pearls or stones, which cosmetic is formed by pressing a mixture of color-coated titanated mica particles, binder and feel enhancer into a continuous solid mass.

BACKGROUND OF THE INVENTION

A new eye shadow has emerged which has caught the fancy of young women. This eye shadow referred to in the trade as "stone eye shadow" is formed of pellets or "stones" of different color pigments which are pressed into an eye shadow base and thus made into finished eye shadow. Many of these stones of different color pigments retain their shape and color without comingling or fusing with other such stones, while other stones fuse with each other. The result is a remarkable array of multi-colored individual and fused pigment stones in a field of eye shadow base.

Until now, stone eye shadow has been prepared by means of a multi-step procedure which involves forming the stones of color pigments, forming the eye shadow base and then pressing the stones into the eye shadow base.

DESCRIPTION OF THE INVENTION

In accordance with the present invention, a unique cosmetic is provided which is in the form of a stone eye shadow and may also be in the form of a facial blusher which is comprised of color-coated titanated mica particles or stones, binder, feel enhancer and preservatives, pressed into a contiguous solid body.

Further, in accordance with the present invention, a method for forming the stone eye shadow of the invention is provided which includes the steps of preparing the color-coated titanated mica particles, mixing such mica particles with dry binder intermediates, coating the particles of the above mixture with wet binder intermediate, to form coated pearls or stones, optionally adding feel enhancer or slip agent, optionally mixing different color coated pearls, and then pressing the pearl mixture to form the stone eye shadow of the invention. The solid body of pressed coated pearls or stones need not be, but may be, used with a separate eye shadow base.

The color-coated titanated mica particles will comprise from about 45 to about 75% and preferably from about 50 to about 65% by weight of the finished stone eye shadow.

The color-coated titanated mica particles are commercially available and are supplied by, for example, Rona Pearl, New Jersey, or Mearl Corp., New York.

They may be formed by mixing pigment particles and titanium dioxide or other particulate pigment carrier such as talc, and then applying a protective coating such as a transparent mica coating over the pigment-carrier particles.

The pigment particles may include any conventional color pigments acceptable for use in cosmetics, such as in eye shadow formulations, such as biron fines, iron oxides, such as black 3068, umber 1985 R (brown), russet C33-5138 (red), cloisonne copper, Nu antique copper, golden bronze, timica copper, Flamenco red 100 and the like.

Examples of the pigment carrier include titanium dioxide, talc and the like.

The transparent mica employed in coating the particles of pigment-carrier mixture include silica minerals such as biotite, muscovite, phlogopite, and/or zinnwaldite.

The dry binder intermediate will comprise from about 10 to about 30% and preferably from about 15 to about 25% of the finished stone eye shadow. It is formed of calcium stearate, zinc stearate, lithium stearate and/or other dry binder with calcium stearate being preferred, in an amount within the range of from about 50 to about 90% and preferably from about 60 to about 80% by weight of the dry binder intermediate, a cleansing agent, antiseptic or preservative such as cetrimonium bromide, imidazolidinyl urea, trisodium ethylene diamine tetraacetic acid and/or butylated hydroxy anisole, cetrimonium bromide being preferred, in an amount within the range of from about 0.1 to about 0.8% and preferably from about 0.3 to about 0.7% by weight of the dry binder intermediate, a thickener which enhances creaminess or laydown of the eye shadow, such as magnesium aluminum silicate, kaolin and/or mica, with magnesium aluminum silicate being preferred, in an amount within the range of from about 1 to about 7% and preferably from about 2 to about 5% by weight of the dry binder intermediate, and a preservative such as methylparaben, propylparaben, imidazolinyl urea, dimethyl dimethoyl hydantoin, N-(3-chloroallyl)hexaminium chloride, benzyl alcohol and/or phenoxy ethanol, with methylparaben or propylparaben being preferred in an amount within the range of from about 0.1 to about 0.8% and preferably from about 0.2 to about 0.6% by weight of the dry binder intermediate.

The wet binder intermediate will comprise from about 5 to about 20% and preferably from about 7 to about 15% by weight of the finished stone eye shadow. It also may include a binder-pigment wetting agent such as hydroxylated lanolin or acetylated lanolin alcohol, in an amount within the range of from about 0 to about 90% and preferably from about 30 to about 60% by weight of the wet binder intermediate; and an oily material to reduce tackiness such as isopropyl myristate, isopropyl palmitate, squalene, oleyl alcohol, mineral oil, liquid lanolin, and/or sesame oil, preferably isopropyl myristate, in an amount within the range of from about 20 to about 90% and preferably from about 30 to about 60% by weight of the wet binder intermediate.

One or more wax bodying agents may optionally be included, such as ozokerite, candelilla, carnauba, cetyl alcohol, lanolin, lanolin alcohol, acetylated lanolin alcohol, synthetic cocoa butter, petrolatum, isopropyl lanolate and/or glyceryl monostearate, in an amount within the range of from about 0 to about 60% and preferably from about 20 to about 40% by weight of the wet binder intermediate.

The stone eye shadow composition of the invention will also include a feel enhancer or slip agent which facilitates laydown of the stone eye shadow and imparts a soft silky feel to the composition and aids in making larger pearls or pellets. Examples of such feel enhancers include volatile silicone, that is cyclomethicone and esters such as isopropyl myristate, isopropyl isostearate or isopropyl palmitate, with volatile silicone being preferred, in an amount within the range of from about 5 to about 25% and preferably from about 10 to about 20% by weight of the finished eye shadow composition.

The following Table sets out preferred compositions of the stone eye shadow of the invention.

| Ingredient | | % by Weight of stone eye shadow product |
|---|---|---|
| I. | Color-coated titanated particles | 50 to 70 |
| II. | Dry binder intermediate | 8 to 15 |
| (a) | dry binder, e.g., Ca stearate, 60 to 80% | % by weight based on weight of dry binder intermediate |
| (b) | cleansing agent or preservative, e.g., cetrimonium bromide, 0.3 to 0.7% | |
| (c) | thickener or laydown enhancer, e.g., Mg Al silicate, 2 to 4.3% | |
| (d) | preservative, e.g., methyl paraben, 0.2 to 0.6% | |
| III. | Wet Binder Intermediate | 6 to 10 |
| (a) | oily material, e.g., isopropyl myristate, 30 to 60% | % by weight based on weight of wet binder intermediate |
| (b) | binder-pigment wetting agent, e.g., hydroxylated lanolin, 20 to 60% | |
| IV. | Feel enhancer, e.g., volatile silicone | 8 to 15 |

In forming the stone eye shadow of the invention, the color-coated titanated mica particles are mixed with dry binder intermediate until a substantially uniform blend is obtained. Thereafter, the wet binder intermediate is slowly mixed with the mica particles-dry binder intermediate mix until the mica particles are coated with dry and wet binder. Thereafter, the feel enhancer, for example, volatile silicone is added to form color pearls or stones which are coated with dry and wet binder intermediates and feel enhancer. The color pearls are sifted through a 40 to 25 mesh sifter. Various color pearls of the same and/or different colors are then mixed together and pressed in a pan at a pressure of from about 800 to about 1500 psi. The result is the formation of the eye shadow of the invention which is formed of a field or a galaxy of pressed color stones of varying colors. The stone eye shadow is easily applied, lays down nicely and provides a pleasant feel to the skin while emitting a dazzling display of eye shadow colors and may be easily spread over and/or worked into an eye shadow base to provide a desired color blend.

The stone blusher of the invention is similar to the stone eye shadow described hereinbefore except that the coated pearls or stones previously formed by mixing color-coated titanated mica pigment particles with dry and wet binder intermediates and feel enhancer are pressed into a conventional blusher base (which will include a desired base color) (employing pressure from about 1000 to about 2000 psi) employing a weight ratio of pearl mixture:blusher base of within the range of from about 1:1 to about 2:1 and preferably from about 1.2:1 to about 1.7:1.

A preferred blusher base will have the following ingredients:

| | Parts by Weight |
|---|---|
| Talc | Q.S. |
| Zn stearate | 0.5 to 3 |
| Ca stearate | 2 to 6 |
| Mica | 8 to 12 |
| Kaolin | 8 to 12 |
| Oat flour | 3 to 7 |
| Preservatives | 0.05 to 0.2 |
| Bismuth oxychloride | 0.05 to 0.2 |
| Pigment | 0.1 to 40 |
| Wet binder | 5 to 10 |

| Wet Binder | % by Weight |
|---|---|
| Acetylated lanolin alcohol | 50 to 70 |
| Sorbitan sesquioleate | 1 to 10 |
| Volatile silicone | 20 to 40 |
| Vitamin E tocopherol | 0 to 0.4 |

The following Examples represent preferred embodiments of the present invention. Unless otherwise indicated, all temperatures are expressed in degrees Centigrade.

EXAMPLE 1

A stone eye shadow in accordance with the present invention having the following composition was prepared as described below.

| Ingredient | | Parts by Weight |
|---|---|---|
| Color-coated titanated mica particles (supplied by Rona Pearl and Mearl) | | 55 |
| a. Cloisonne blue stone - 40% | | Based on by weight of color-coated titanated mica particles |
| b. Red stone - 14% | | |
| c. Gold sparkle stone - 14% | | |
| d. Supergreen stone - 32% | | |
| Dry binder intermediate | | 20 |
| a. Ca stearate (binder) | 15.0 | |
| b. Cetrimonium bromide (preservative) | 0.5 | |
| c. Methyl paraben (preservative) | 0.5 | |
| d. MgAlSiO₃ (promote creaminess) | 4.0 | |
| | 20.0 parts by weight | |
| Wet binder intermediate | | 10 |
| Isopropyl myristate (reduce,tackiness) | 10 parts by weight | |
| Volatile silicone (feel enhancer) | | 15 |
| | | 100 |

The various color-coated titanate mica particles were commercially available.

The dry binder intermediate was formed by mixing the various ingredients listed above in a P-K blender for about 15 minutes to form a uniform mix which was passed through a micropulverizer (0.013 inch mesh), two times.

The liquid binder intermediate was formed by mixing while heating the mix to about 80° C.

In forming the stone eye shadow of the invention, the color-coated titanated mica particles were mixed in a P-K blender with dry binder intermediate for about 5 minutes until a substantially uniform blend was obtained. Thereafter, the wet binder intermediate was slowly mixed with the mica particle-dry binder intermediate mix until the mica particles were coated with dry and wet binder. Thereafter, the volatile silicone feel enhancer was added to form color pearls or stones which are coated with dry and wet binder intermediates and feel enhancer. The so-formed coated pearls were sifted through a 30 mesh sifter. Various coated pearls of the same and/or different colors were then mixed together and pressed in a pan at a pressure of from about 800 to about 1500 psi. The result is the formation of the eye shadow of the invention which was formed of a field of galaxy of pressed color stones of varying colors. The stone eye shadow was easily applied, laid down nicely and provided a pleasant feel to the skin while emitting a dazzling display of eye shadow colors. The eye shadow is easily blended into the skin or blended with a previously applied eye shadow base.

EXAMPLE 2

A stone blusher in accordance with the present invention having the following composition was prepared as described below.

| Ingredient | % by Weight of Final Product |
|---|---|
| Blusher base-parts by weight | 70 |
| Talc - 43.5 | |
| Zn stearate - 1 | |
| Ca stearate - 3 | |
| Mica - 20 | |
| Kaolin - 10 | |
| Oat flour - 5 | |
| Methylparaben - 0.1 | |
| Cetrimonium bromide - 0.1 | |
| Benzophenone-3 - 0.1 | |
| Bismuth oxychloride - 5 | |
| Pigment - 5 | |
| Acetylated lanolin alcohol - 4.5 | |
| Sorbitan sesquioleate - 0.4 | |
| Volatile silicone - 2.1 | |
| Vitamin E tocopherol - 0.2 | |
| Stone particles | |
| As per Example 1 | 30 |
| | 100% |

The stone blusher is prepared by pressing the stone particles, prepared as described in Example 1, into the blusher base. The result is a beautiful non-uniform blend of stone particles dispersed throughout the blusher base—a veritable palate of colors.

To use, blusher base may be separately applied and thereafter stone-blusher non-uniform blend may be applied and blended into the base to desired color. Since the stone-blusher blend will not be uniform in color dispersion, different portions of such blend may be applied to achieve different color results.

What is claimed is:

1. A stone eye shadow formulation prepared by the method which comprises providing color-coated titanated mica particles, mixing the color-coated titanated mica particles with a dry binder intermediate, coating particles of the above mixture with wet binder intermediate, adding feel enhancer to form color-coated pearls, sifting the color-coated pearls and mixing together color-coated pearls of different color and then pressing the so-formed color-coated pearls to form a contiguous solid body of eye shadow containing particles of color dispersed therein.

2. The eye shadow formulation as defined in claim 1 wherein the dry binder intermediate is comprised of a dry binder, preservative and thickener-cream enhancer and the wet binder intermediate is comprised of a binder, bodying agent and tackiness reducer.

3. The eye shadow formulation as defined in claim 2 wherein the dry binder in the dry binder intermediate is calcium stearate, lithium stearate, zinc stearate, aluminum stearate or mixtures thereof, preservative in the dry binder intermediate is cetrimonium bromide, methyl paraben, propyl paraben, imidazolinyl urea, dimethyl dimethoyl hydantoin, N-(3chloroallyl)-hexaminium chloride, benzyl alcohol or phenoxyethanol, and the thickener-cream enhancer in the dry binder intermediate is magnesium aluminum silicate, kaolin or mica.

4. The eye shadow formulation as defined in claim 2 wherein the binder in the wet binder intermediate is hydroxylated lanolin, or acetylated lanolin alcohol, the tackiness reducer in the wet binder intermediate is isopropyl myristate, isopropyl palmitate, squalene, oleyl alcohol, castor oil, mineral oil, liquid lanolin or sesame oil.

5. The eye shadow formulation as defined in claim 1 wherein the feel enhancer is volatile silicone, isopropyl myristate, isopropyl isostearate or isopropyl palmitate.

6. The eye shadow formulation as defined in claim 1 wherein the color-coated titanated mica particles comprise from about 45 to about 75% by weight of the eye shadow, the dry binder intermediate comprises from about 10 to about 30% by weight of the eye shadow and the wet binder intermediate comprises from about 5 to about 20% by weight of the eye shadow, and the feel enhancer comprises from about 5 to about 25% by weight of the eye shadow.

7. The eye shadow formulation as defined in claim 1 wherein the dry binder intermediate is comprised of calcium stearate, preservative and magnesium aluminum silicate, and the wet binder intermediate is comprised of hydroxylated lanolin and isopropyl myristate, and the feel enhancer is volatile silicone.

8. A method for forming a stone eye shadow which comprises providing color-coated titanated mica particles, mixing the color-coated titanated mica particles with a dry binder intermediate, coating particles of the above mixture with wet binder intermediate, adding feel enhancer to form color-coated pearls, sifting the color-coated pearls and mixing together color-coated pearls of different color and then pressing the so-formed color-coated pearls to form a contiguous solid body of eye shadow containing particles of color dispersed therein.

9. A blusher cosmetic formulation prepared by the method which comprises providing color-coated titanated mica particles, mixing the color-coated titanated mica particles with a dry binder intermediate, coating particles of the above mixture with a wet binder intermediate, adding feel enhancer to the form color-coated pearls, sifting the color-coated pearls and mixing together color-coated pearls of different color and then pressing the so-formed color-coated pearls to form a contiguous solid body of blusher cosmetic containing particles of color dispersed therein.

10. The blusher cosmetic formulation as defined in claim 9 wherein the color-coated pearls are employed in a weight ratio to blusher base of within the range of from about 1:1 to about 2:1.

* * * * *